United States Patent
Sangu (10) Patent No.: US 10,983,592 B2
(45) Date of Patent: Apr. 20, 2021

(54) EYEBALL-TILT POSITION DEVICE AND APPARATUS INCLUDING SAME

(71) Applicant: Suguru Sangu, Kanagawa (JP)

(72) Inventor: Suguru Sangu, Kanagawa (JP)

(73) Assignee: Ricoh Company, Ltd., Tokyo (JP)

( * ) Notice: Subject to any disclaimer, the term of this patent is extended or adjusted under 35 U.S.C. 154(b) by 28 days.

(21) Appl. No.: 16/292,435

(22) Filed: Mar. 5, 2019

(65) Prior Publication Data

US 2019/0286228 A1   Sep. 19, 2019

(30) Foreign Application Priority Data

Mar. 13, 2018   (JP) .............................. JP2018-045947

(51) Int. Cl.
| | | |
|---|---|---|
| *H04N 5/228* | (2006.01) | |
| *G06F 3/01* | (2006.01) | |
| *G02B 26/10* | (2006.01) | |
| *A61B 3/113* | (2006.01) | |
| *A61B 3/15* | (2006.01) | |
| *G02B 27/01* | (2006.01) | |

(Continued)

(52) U.S. Cl.
CPC .............. *G06F 3/013* (2013.01); *A61B 3/113* (2013.01); *A61B 3/15* (2013.01); *G02B 26/101* (2013.01); *G02B 27/0172* (2013.01); *G02B 26/0833* (2013.01); *G02B 27/0093* (2013.01); *G02B 2027/014* (2013.01); *G02B 2027/0178* (2013.01); *G06T 19/006* (2013.01); *G06T 2207/30041* (2013.01); *G06T 2207/30201* (2013.01)

(58) Field of Classification Search
CPC ........... A61B 3/113; A61B 3/15; G06F 3/013; G02B 26/101; G02B 26/0833; G02B 27/0172; G02B 27/0093; G02B 2027/014; G02B 2027/0178; G06T 19/006; G06T 2207/30041; G06T 2207/30201
USPC .......................... 348/78, 169, 208.14, 222.1
See application file for complete search history.

(56) References Cited

U.S. PATENT DOCUMENTS

| | | | |
|---|---|---|---|
| 2004/0190136 A1* | 9/2004 | Kanai ..................... | G02C 7/088 359/407 |
| 2006/0177959 A1* | 8/2006 | Boettiger .......... | H01L 27/14627 438/70 |

(Continued)

FOREIGN PATENT DOCUMENTS

| | | |
|---|---|---|
| JP | 7-128579 | 5/1995 |
| JP | 2015-187713 | 10/2015 |
| JP | 2018-063365 | 4/2018 |

OTHER PUBLICATIONS

Oshima, S. "Optical Mechanism of an Eye" Journal of the Japan Society of Precision Engineering, 1961, 7 Pages (with partial English translation).

*Primary Examiner* — Usman A Khan (74) *Attorney, Agent, or Firm* — Oblon, McClelland, Maier & Neustadt, L.L.P.

(57) ABSTRACT

An eyeball-tilt detecting device for detecting a tilt position of an eyeball, including: a light source array including a plurality of light emitting sections that emit light having directivity; an optical spot position detection element configured to detect an optical spot position of light reflected from an eyeball to output a detection signal; and processing circuitry configured to calculate a tilt position of the eyeball based on the detection signal output from the optical spot position detection element.

15 Claims, 10 Drawing Sheets

(51) Int. Cl.
    *G02B 27/00* (2006.01)
    *G06T 19/00* (2011.01)
    *G02B 26/08* (2006.01)

(56) References Cited

U.S. PATENT DOCUMENTS

| | | | | |
|---|---|---|---|---|
| 2009/0268025 | A1* | 10/2009 | Hiramaki | B60K 35/00 |
| | | | | 348/148 |
| 2009/0299347 | A1* | 12/2009 | Vogler | A61F 9/008 |
| | | | | 606/5 |
| 2013/0044130 | A1* | 2/2013 | Geisner | G06F 3/002 |
| | | | | 345/633 |
| 2013/0335546 | A1* | 12/2013 | Crane | H04N 5/2251 |
| | | | | 348/78 |
| 2014/0098198 | A1* | 4/2014 | Lee | G06F 3/013 |
| | | | | 348/48 |
| 2014/0111632 | A1* | 4/2014 | Huang | G06F 3/013 |
| | | | | 348/78 |
| 2015/0260982 | A1 | 9/2015 | Sangu | |
| 2016/0166146 | A1 | 6/2016 | Sarkar | |
| 2017/0140224 | A1* | 5/2017 | Wilson | G06K 9/00604 |

* cited by examiner

EYEBALL-TILT POSITION DEVICE AND APPARATUS INCLUDING SAME

CROSS-REFERENCE TO RELATED APPLICATIONS

This patent application is based on and claims priority pursuant to 35 U.S.C. § 119(a) to Japanese Patent Application No. 2018-045947, filed on Mar. 13, 2018, in the Japan Patent Office, the entire disclosure of which is hereby incorporated by reference herein.

BACKGROUND

Technical Field

The present invention relates to an eyeball-tilt position detecting device, and an apparatus including the eyeball-tilt position detecting device such as a display device and an eye examination apparatus.

Description of the Related Art

In recent years, technologies and products related to virtual reality (VR) and augmented reality (AR) have attracted attention. In particular, AR technology is expected to be applied to industrial fields as means for displaying digital information in real space. In view of the fact that person who utilizes the AR technology visually acquires most of cognitive information, eyeglass-type image display apparatuses that can be used in an action (working) environment have been developed.

As one of such eyeglass-type image display apparatuses, there has been known an eyeglass-type image display apparatus that employs a retina rendering method of directly rendering images on the retina of person using a laser. According to the retina rendering method, by superimposing a focus-free image on viewing information, digital information can be displayed on the retina while the viewpoint is placed on the outside world and recognized by person.

Meanwhile, in the eyeglass-type image display apparatus that employs the retinal rendering method using a laser, the following problem occurs. That is, as the size of a cornea or a pupil is restricted, vignetting of the laser occurs in the peripheral portion of the cornea or pupil in an action (working) environment that requires eye movements, so that a predetermined image may not be rendered at a predetermined position.

To solve such a problem, eye tracking technologies are disclosed for the purpose of detecting the position of the cornea and feedbacking that position to the rendering position of an image. The eye tracking technologies include a micro electro mechanical systems (MEMS) mirror for scanning lasers on an eyeball, a photodetector for detecting the intensity of reflected light, and an electronic circuit for estimating the position of the cornea on the eyeball from the intensity detected.

However, as the technologies described above include a movable structure such as a MEMS mirror, the detection precision of an eyeball tilt position such as a position of a cornea may be degraded due to vibration and external impact.

SUMMARY

Example embodiments of the present invention include an eyeball-tilt detecting device for detecting a tilt position of an eyeball, including: a light source array including a plurality of light emitting sections that emit light having directivity; an optical spot position detection element configured to detect an optical spot position of light reflected from an eyeball to output a detection signal; and processing circuitry configured to calculate a tilt position of the eyeball based on the detection signal output from the optical spot position detection element.

BRIEF DESCRIPTION OF THE DRAWINGS

A more complete appreciation of the disclosure and many of the attendant advantages and features thereof can be readily obtained and understood from the following detailed description with reference to the accompanying drawings, wherein.

The accompanying drawings are intended to depict embodiments of the present disclosure and should not be interpreted to limit the scope thereof. The accompanying drawings are not to be considered as drawn to scale unless explicitly noted.

DETAILED DESCRIPTION

The terminology used herein is for the purpose of describing particular embodiments only and is not intended to be limiting of the present invention. As used herein, the singular forms "a", "an" and "the" are intended to include the plural forms as well, unless the context clearly indicates otherwise.

In describing embodiments illustrated in the drawings, specific terminology is employed for the sake of clarity. However, the disclosure of this specification is not intended to be limited to the specific terminology so selected and it is to be understood that each specific element includes all technical equivalents that have a similar function, operate in a similar manner, and achieve a similar result.

Embodiments will be described hereinafter with reference to the drawings. In the drawings, like parts are given like reference numerals and overlapping descriptions will be omitted.

In the embodiments, the position of a pupil or a cornea of an eyeball is an example of the eyeball tilt position to be detected by an eyeball-tilt-position detecting device. Accordingly, in the following, a pupil position detector will be described as an example of the eyeball-tilt-position detecting device. Further, a case where the pupil position detector is mounted on an eyeglass-type support (such as a frame) will be described as an example.

While the embodiments describe a pupil position detector for a right eyeball of person as an example, the pupil position detector may also be used for a left eyeball. Alternatively, two pupil position detectors may be provided and used for both eyeballs.

First Embodiment

Figure 1:
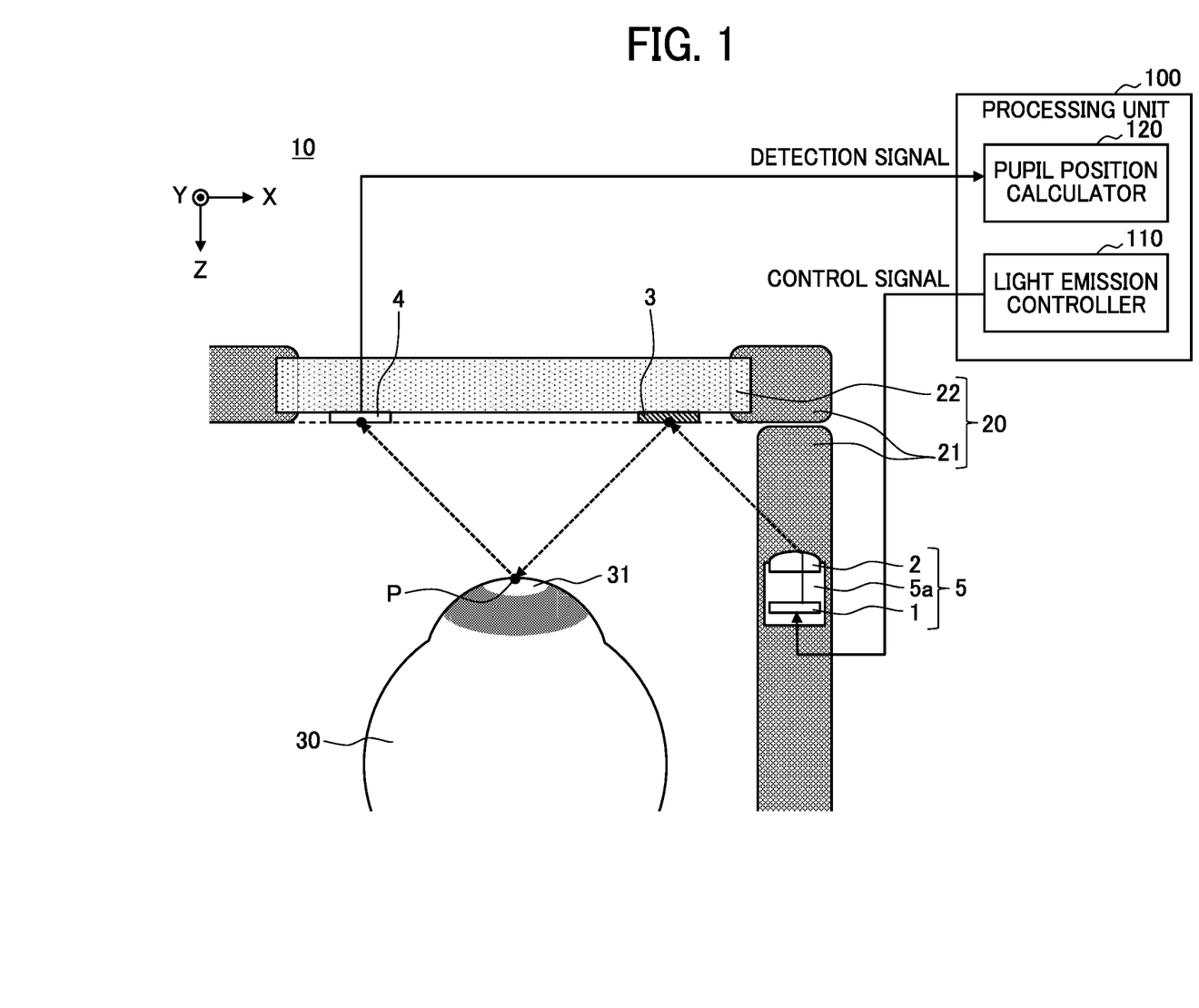
FIG. 1 is a view illustrating an example of a configuration of a pupil position detector according to a first embodiment.

FIG. 1 is a view illustrating an example of a configuration of a pupil position detector according to the present embodiment. Arrows in FIG. 1 indicate X, Y, and Z directions, respectively.

In FIG. 1, a pupil position detector 10 includes a light source array 1, a lens 2, a plane mirror 3, an optical spot position detection element 4, and a processing unit 100. The light source array 1 and the lens 2 are provided in an eyeglass frame 21 of an eyeglass-type support 20. The plane mirror 3 and the optical spot position detection element 4 are provided on an eyeglass lens 22 of the eyeglass-type support 20. The processing unit 100 includes a light emission controller 110 and a pupil position calculator 120.

The light source array 1 includes a plurality of light emitting sections that are two-dimensionally arranged in a plane. In this disclosure, "a plurality of light emitting sections" is synonymous with "a plurality of light emitting points" or "a plurality of light emitting elements".

Each light emitting section emits laser light having directivity upward in the drawing. The light source array 1 is, for example, a vertical cavity surface emitting laser (VCSEL) whose emission direction is upward in the drawing. However, the light source array 1 is not limited to the VCSEL. For example, the light source array 1 may be configured by two-dimensionally arranging a plurality of LDs (semiconductor lasers; laser diodes) that emit laser beams having directivity in a plane.

The wavelength of light emitted from the light source array 1 is preferably the wavelength of near-infrared light, which is invisible light, so as not to hinder the visibility of person whose pupil position is to be detected. The wavelength is not limited to the wavelength of near-infrared light, and may be the wavelength of visible light.

The lens 2 deflects light emitted from the light source array 1 in a predetei mined direction. The lens 2 is, for example, a convex lens, and refracts passing light to deflect the passing light in a predetermined direction. The light source array 1 and the lens 2 are disposed on a same substrate 5a and integrated to constitute a light distribution module 5. The light distribution module 5 is disposed on a stably stationary support such as the eyeglass frame 21 of the eyeglass-type support 20.

Light deflected by the lens 2 is reflected to an eyeball 30 by the plane mirror 3. The plane mirror 3 is disposed on the eyeglass lens 22 of the eyeglass-type support 20. By the deflection by the lens 2 and the reflection by the plane mirror 3, light from the light source array 1 is incident on the center of a pupil 31 of the eyeball 30 in normal vision at a predetermined angle. The lens 2 and the plane mirror 3 have a function of deflecting light from the light source array 1 and causing the light to be incident on the eyeball 30. The lens 2 and the plane mirror 3 are examples of a light deflector.

The light deflector is not limited to the lens 2 and the plane mirror 3. The light deflector may be any member or a combination of any members that can cause light from the light source array 1 to be incident on the eyeball at a predetermined angle. By using, as the light deflector, one of a microlens array, a concave curved mirror, a hologram diffraction element, a prism array, and a diffraction grating in addition to the convex lens described above, or a combination of two or more of these components mentioned above, it is possible to extend a pupil detection range, downsize the pupil position detector, and reduce a load of assembling the pupil position detector 10. Other examples of the light deflector will be described in detail in a third embodiment.

The pupil surface (corneal surface) is a transparent body containing moisture and commonly has a reflectance of approximately 2% to 4%. Light incident near the pupil 31 is reflected at a reflection point P on the pupil surface (corneal surface) of the eyeball 30, and reflected light is incident on the optical spot position detection element 4. The optical spot position detection element 4 is, for example, a two-dimensional position sensitive detector (PSD).

The PSD detects the direction of a normal vector of the reflection point, that is, a three-dimensional shape. The pupil center position is estimated by comparing the three-dimensional shape detected to an eyeball model.

The two-dimensional PSD detects current values in two directions orthogonal to each other in a light receiving surface based on the distance from the position of light incident on the light receiving surface to an electrode, calculates the position of incident light from the ratio of current values in the two directions, and outputs the position of incident light. The two-dimensional PSD can detect the position of incident light independently of the intensity of the incident light. For this reason, if there is a difference in the amount of reflected light due to the reflection position on the eyeball 30, it is possible to perform detection with high sensitivity without being affected by the difference in the amount of reflected light. Unlike a case of using an image sensor such as a charge coupled device (CCD) or a complementary metal-oxide-semiconductor (CMOS) as the optical spot position detection element 4, the two-dimensional PSD does not require complicated image processing for position detection, thus reducing a processing load.

However, the optical spot position detection element 4 is not limited to the two-dimensional PSD. One-dimensional PSDs capable of detecting the position of incident light in the X direction may be arranged in the Y direction, or one-dimensional PSDs capable of detecting the position of incident light in the Y direction may be arranged in the X direction, for the purpose of detecting the position of incident light in an XY plane. In this case, the one-dimensional PSD is inexpensive compared to the two-dimensional PSD or the like, and thus it is possible to reduce the cost of the pupil position detector 10.

Alternatively, the image sensor such as CCD or CMOS may be used as the optical spot position detection element 4, and the position of light spot may be detected or estimated by image processing based on the spatial intensity distribution of light incident on an imaging surface.

The position of light incident on the light receiving surface of the optical spot position detection element 4 is an example of optical spot position of reflected light from eyeball.

The light emission controller 110 included in the processing unit 100 is electrically connected to the light source array 1 and transmits a control signal to the light source array 1. Using the control signal, the light emission controller 110 controls each light emitting section of the light source array 1 to emit light and the time for light emission. That is, the light emission time of the light emitting section changes at a predetermined time. The light emission controller 110 can thus change the incident angle of light on the eyeball 30 in a time series.

The pupil position calculator 120 is electrically connected to the optical spot position detection element 4 and receives a detection signal output from the optical spot position detection element 4 based on the position of light incident on the light receiving surface of the optical spot position detection element 4. The pupil position calculator 120 calculates the position of the pupil 31 based on the detection signal.

When the direction of reflected light from the eyeball 30 changes by eye movements such as the rotation of the eyeball 30, reflected light may deviate from the light receiving surface of the optical spot position detection element 4. To prevent such a case, the light emission controller 110 successively or selectively changes the light emitting sections of the light source array 1 to emit light. When the light emitting section changes, the position of light emission in the plane where the light emitting sections are arranged in the light source array 1 changes accordingly, and thus the incident angle of light incident on the eyeball 30 via the lens 2 and the plane mirror 3 also changes. As the incident angle of light on the eyeball 30 changes, the position of light reflected by the eyeball 30 and incident on the light receiving surface of the optical spot position detection element 4 changes accordingly. By changing the light emitting section of the light source array 1 to emit light according to the movement of the eyeball 30, it is possible to prevent light reflected from the eyeball 30 from deviating from the light receiving surface of the optical spot position detection element 4.

The signal detected by the optical spot position detection element 4 indicates a change in the light reflection position on the eyeball 30. The pupil position calculator 120 calculates the rotation angle and pupil position of the eyeball 30 based on the detection signal from the optical spot position detection element 4.

Figure 2A:
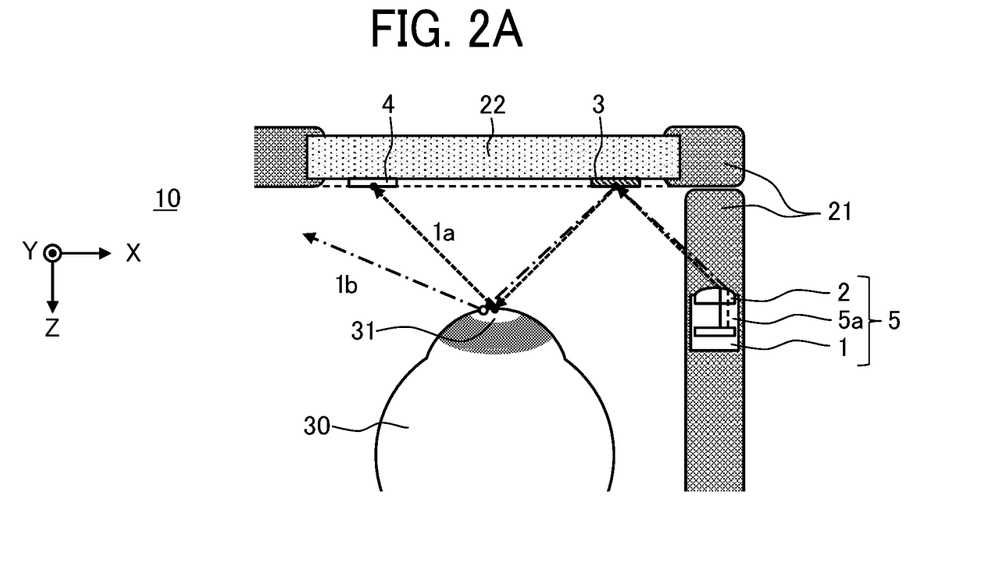
FIGS. 2A and 2B are views explaining an example of a pupil position detection operation by the pupil position detector according to the first embodiment.
Figure 2B:
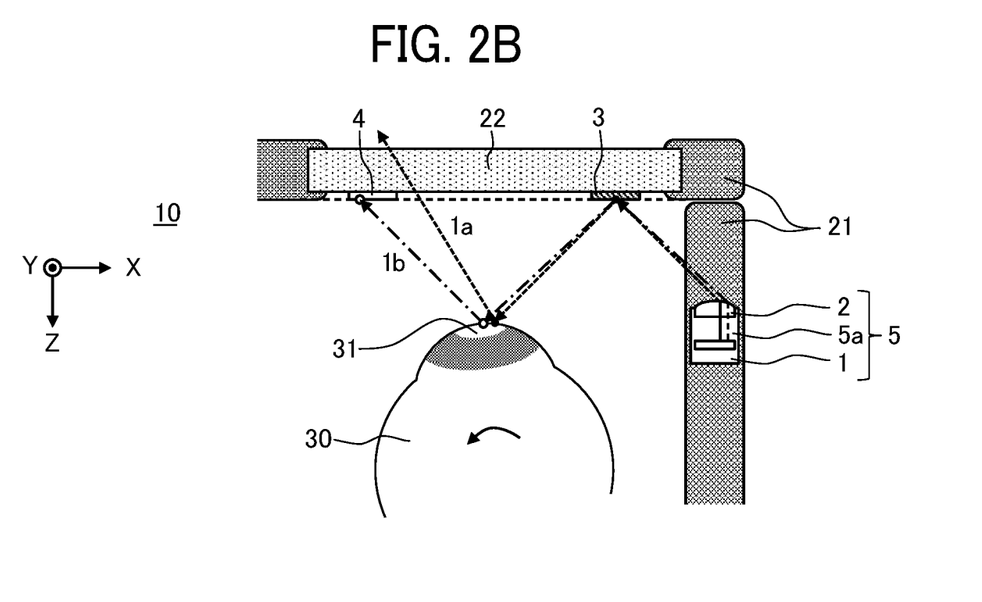

FIGS. 2A and 2B are views explaining an example of a pupil position detection operation by the pupil position detector 10. FIGS. 2A and 2B illustrate the behavior of light emitted from two light emitting sections at different positions in the light source array 1. Light 1a from one light emitting section is indicated by a dotted line and light 1b from the other light emitting section is indicated by a chain line. FIG. 2A illustrates a state where the eyeball 30 is in normal vision, that is, faces front, and FIG. 2B illustrates a state where the eyeball 30 is rotated.

In FIG. 2A, the light 1a indicated by the dotted line is reflected by the eyeball 30 and incident near the center of the light receiving surface of the optical spot position detection element 4. The optical spot position detection element 4 can thus detect a change in the incident position of the light 1a on the light receiving surface according to the rotation of the eyeball 30. The pupil position calculator 120 can calculate the position of the pupil 31 based on a detection signal from the optical spot position detection element 4. Meanwhile, the light 1b indicated by the chain line is reflected by the eyeball 30 but is not incident the light receiving surface of the optical spot position detection element 4. Consequently, the light 1b does not contribute to the detection signal of the optical spot position detection element 4. The pupil position calculator 120 cannot calculate the position of the pupil 31.

On the other hand, as illustrated in FIG. 2B, when the eyeball 30 is rotated largely as compared to FIG. 2A, the light 1a incident on the light receiving surface of the optical spot position detection element 4 in normal vision is deviated from the light receiving surface of the optical spot position detection element 4 and does not contribute to the detection signal of the optical spot position detection element 4. Consequently, the pupil position calculator 120 cannot calculate the position of the pupil 31. Meanwhile, the light 1b is incident near the center of the light receiving surface of the optical spot position detection element 4. The optical spot position detection element 4 can thus detect a change in the incident position of the light 1b on the light receiving surface according to the rotation of the eyeball 30. The pupil position calculator 120 can calculate the position of the pupil 31 based on the detection signal from the optical spot position detection element 4.

With light from one light emitting section, the movement of the eyeball 30 is detected only in a limited angle range. In the present embodiment, by changing the light emitting section of the light source array 1, the incident angle of light on the eyeball 30 is changed and thus the detection range of the movement of the eyeball 30 is extended. It is thus possible to extend the detection range of the position of the pupil 31.

The light emitting section of the light source array 1 is changed in a time series in response to a control signal from the light emission controller 110 according to the movement of the eyeball 30. By controlling the light emitting section according to (by following) the movement of the eyeball 30, it is possible to improve light use efficiency and reduce the estimation time. However, such an action does not need to be performed according to eye movements. For example, it is also possible to acquire the fluttering position of the eyeball by raster-scanning the positions of the light emitting sections at regular time intervals independently of the eye movements.

FIGS. 2A and 2B illustrate only light emitted from two light emitting sections for the sake of simplicity. In the present embodiment, more light emitting sections of the light source array 1 can be used according to the movement of the eyeball 30. In this case, the number and positions of the light emitting sections in the light source array 1 are optimized according to the size of the light receiving surface of the optical spot position detection element 4 and the size of the eyeball, for the purpose of properly detecting the position of the pupil 31.

Figure 3:
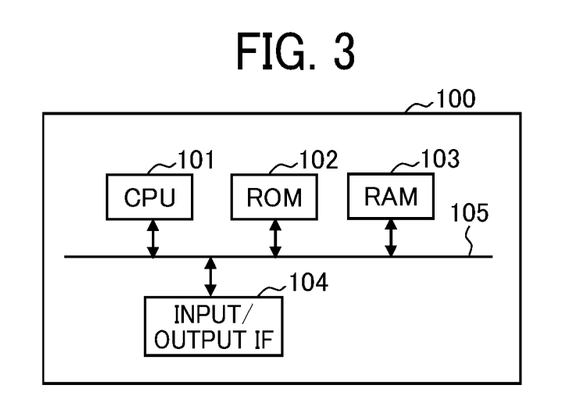
FIG. 3 is a schematic block diagram illustrating an example of a hardware configuration of a processing unit according to the first embodiment.

FIG. 3 is a block diagram illustrating an example of a hardware configuration of the processing unit 100 according to the present embodiment.

The processing unit 100, which is implemented by the general-purpose computer, includes a central processing unit (CPU) 101, a read only memory (ROM) 102, a random access memory (RAM) 103, and an input/output interface (I/F) 104. These components are connected to each other via a system bus 105.

The CPU 101 generally controls an operation of the processing unit 100. The CPU 101 also performs a process of calculating the position of the pupil 31 based on a detection signal from the optical spot position detection element 4.

The CPU 101 executes a program that is stored in the ROM 102 or the like by using the RAM 103 as a work area to execute the control described above and perform the process described above, thus achieving various functions to be described later. Note that some or all of the functions of the CPU 101 may be achieved by hardware using wired logic such as an application specific integrated circuit (ASIC) or a field-programmable gate array (FPGA).

The input/output I/F 104 is an interface for connecting the processing unit 100 to an external apparatus such as a personal computer (PC) or video equipment.

Figure 4:
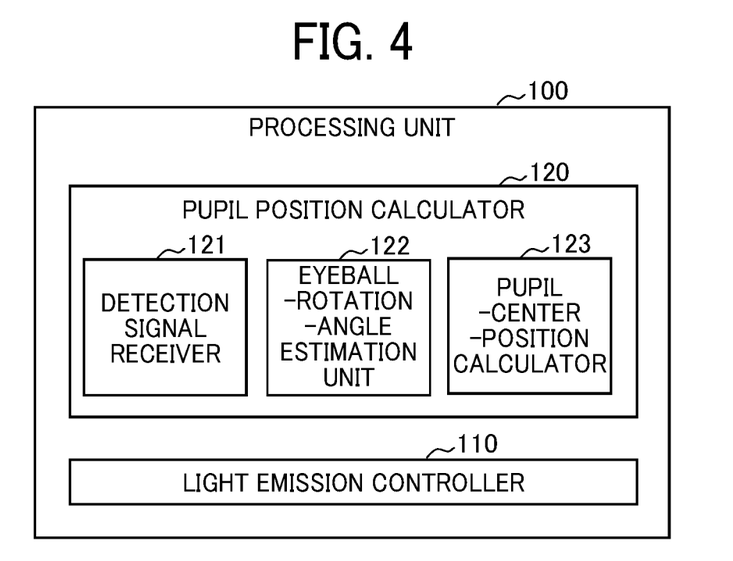
FIG. 4 is a functional block diagram illustrating an example of components included in the processing unit according to the first embodiment.

FIG. 4 is a functional block diagram illustrating an example of components included in the processing unit 100 according to the present embodiment. The functional blocks illustrated in FIG. 4 are conceptual and do not necessarily need to be physically configured as illustrated in FIG. 4. Some or all of the functional blocks may be configured by functionally or physically distributing or combining these functional blocks in arbitrary units. Each processing function performed in each functional block may be entirely or partially achieved by a program executed by the CPU 101 described above, or may be achieved as hardware by wired logic.

As described above, the processing unit 100 includes the light emission controller 110 and the pupil position calculator 120. The function of the light emission controller 110 has been described above. The pupil position calculator 120 includes a detection signal receiver 121, an eyeball-rotation-angle estimation unit 122, and a pupil-center-position calculator 123.

The detection signal receiver 121 receives a detection signal output from the optical spot position detection element 4 and outputs the detection signal to the eyeball-rotation-angle estimation unit 122.

The eyeball-rotation-angle estimation unit 122 estimates the rotation angle of the eyeball 30 based on the detection signal from the optical spot position detection element 4 and outputs the rotation angle estimated to the pupil-center-position calculator 123.

The pupil-center-position calculator 123 calculates the center position of the pupil 31 based on the rotation angle of the eyeball 30.

Figure 5:
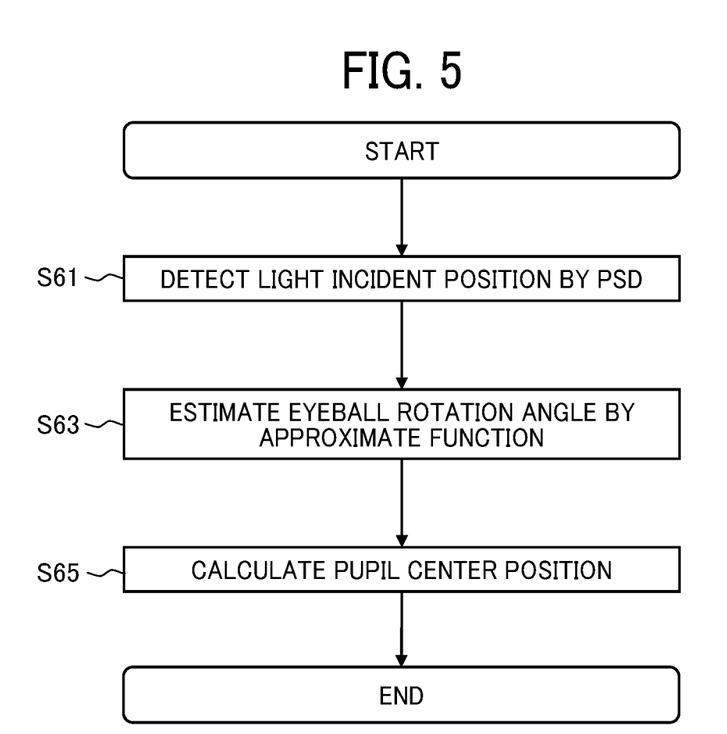
FIG. 5 is a flowchart illustrating an example of a process performed by a pupil position calculator according to the first embodiment.

FIG. 5 is a flowchart illustrating an example of a process performed by the pupil position calculator 120 according to the present embodiment.

Prior to step S61, an angle at which light emitted from the light source array 1 is incident on the eyeball 30 is designed and an equation for calculating the rotation angle of the eyeball 30 is determined as a preparation for calculating the pupil position.

The equation for calculating the rotation angle of the eyeball 30 is the equation of a linear function or a quadratic function. However, the equation is not limited to these equations mentioned above. Any equation may be used as long as it is an equation for determining the rotation angle from the light incident angle designed and the incident position of reflected light on the optical spot position detection element. The equation of the quadratic function is used as a simple approximate expression in a simulation.

In designing the angle at which light is incident on the eyeball 30, a model of the surface of the eyeball 30 is used, such as a common model of the surface of the eyeball as described in OSHIMA Sukeyuki, "Optical Mechanism of an Eye", Journal of the Japan Society of Precision Engineering: 27-11, 1961, pp. 38-43, or any other desired model.

The plane mirror 3 (see FIGS. 1 and 2) is disposed at the focal point of light emitted from the light source array 1. Light reflected by the plane mirror 3 is incident on the eyeball 30. The light incident on the eyeball 30 is reflected by the eyeball 30 that is rotated by a predetermined angle and propagated to the optical spot position detection element 4. The angle of light to be incident on the eyeball 30 is calculated and designed in advance by ray tracing calculation or the like so that propagating light is incident on the center position of the light receiving surface of the optical spot position detection element 4.

The incident position of light on the light receiving surface of the optical spot position detection element 4 can be theoretically analyzed based on the incident angle of light on the eyeball 30, the light reflection position of the eyeball 30, and the inclination of the contact surface of the surface of the eyeball 30. An inverse operation expression (approximate expression) for estimating the rotation angle of the eyeball 30 is determined from the solution of the theoretical analysis through polynomial approximation.

The preparation for calculating the pupil position prior to step S61 in FIG. 5 has been described above. The angle of light to be incident on the eyeball 30 and the inverse operation expression for estimating the rotation angle of the eyeball 30 are stored in a memory such as the ROM 102 of the processing unit 100, and referred to and used when the light emission controller 110 controls light emission and when the pupil position calculator 120 calculates the pupil position.

In FIG. 5, the light emission controller 110 first causes at least one of the light emitting sections of the light source array 1 to emit light at a predetermined time, which is determined according to the incident angle of light designed in advance. The optical spot position detection element 4 detects the position where light emitted from the light source array 1 and reflected by the eyeball 30 is incident on the light receiving surface of the optical spot position detection element 4 and outputs the position to the processing unit 100. In the processing unit 100, the detection signal receiver 121 included in the pupil position calculator 120 receives a detection signal from the optical spot position detection element 4 (step S61). The detection signal receiver 121 outputs the detection signal to the eyeball-rotation-angle estimation unit 122.

Next, the eyeball-rotation-angle estimation unit 122 substitutes the input detection signal (position data) for the inverse operation expression described above to calculate an eyeball rotation angle (step S63). The eyeball-rotation-angle estimation unit 122 outputs the eyeball rotation angle calculated to the pupil-center-position calculator 123.

Based on the input eyeball rotation angle, the pupil-center-position calculator 123 calculates the center position of the pupil using the model of the surface of the eyeball (step S65).

In this way, the position of the pupil 31 on the eyeball 30 can be detected.

Figure 6A:
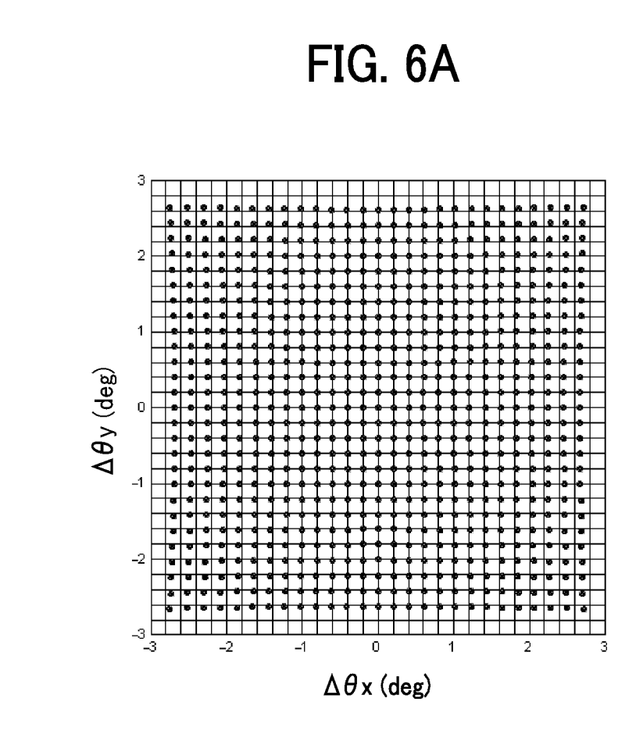
FIGS. 6A and 6B are graphs explaining a numerical simulation carried out to verify the principle of pupil position detection in the pupil position detector according to the first embodiment.
Figure 6B:
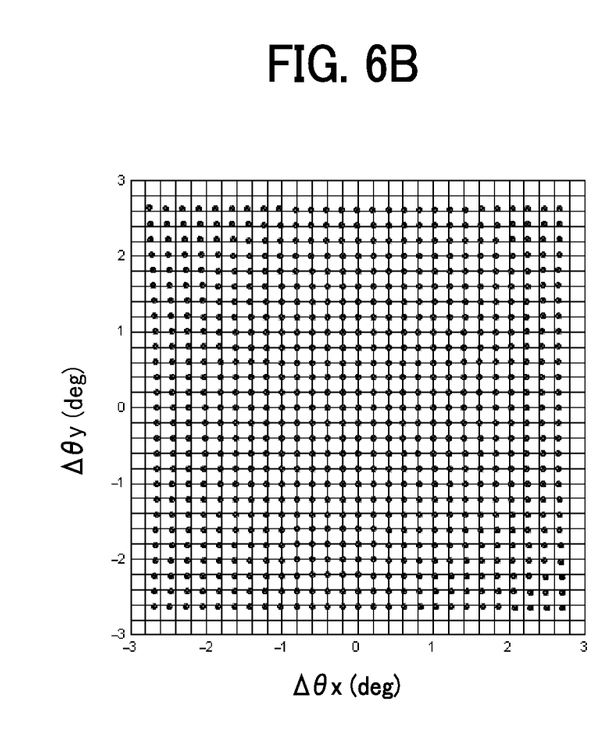

FIGS. 6A and 6B are graphs explaining a numerical simulation carried out to verify the principle of pupil position detection in the pupil position detector 10 according to the present embodiment.

It is assumed in this numerical simulation that in FIG. 1, the plane mirror 3 and the optical spot position detection element 4 are disposed in a plane that is separated from the eyeball 30 by 10 mm in an −Z-axis direction. A case where the rotation angle of the eyeball 30 is changed at 5 points in the X direction and at 3 points in the Y direction at intervals of 5° is defined as the reference angle (θx, θy) of the eyeball 30.

In FIGS. 6A and 6B, the horizontal axis represents a variation in the eyeball rotation angle in the X direction and the vertical axis represents a variation in the eyeball rotation angle in the Y direction. These variations are based on incident angles (angle variation (0, 0)) obtained by changing the rotation angle at 5 points in the X direction and at 3 points in the Y direction at intervals of 5°.

In the numerical simulation, the exit angle (the reflection angle at the plane mirror 3) of light, which is reflected by the eyeball 30 to be incident on the center of the optical spot position detection element 4, from the plane mirror 3 is numerically calculated for each reference angle of the eyeball 30. The center of the optical spot position detection element 4 is expressed as coordinates (0, 0).

In addition, the difference (Δθx, Δθy) between each exit angle of light and the reference angle (θx, θy) of the eyeball 30 is represented by a quadratic function using an inverse operation expression that estimates the rotation angle from an incident position (x, y) on the light receiving surface of the optical spot position detection element 4, and coefficients of the quadratic function are numerically calculated by Taylor series.

FIG. 6A is a graph showing estimation results of the rotation angle of the eyeball 30 when the reference angle is (θx, θy)=(0°,0°), that is, when normal vision is set to the reference angle. In the graph of FIG. 6A, a lattice point indicates the actual rotation angle of the eyeball 30 and a dot indicates an estimated position. When the rotation angle of the eyeball 30 is small, good matches are found between the lattice points and the dots. In this case, in a range of |Δθx|≤2.5°, an error is within approximately up to 0.1°. Note that numerical value 2.5° is a half of 5°, which is an interval of changing the reference angle, and is a condition for eliminating an area where light is not detected. As it is assumed that the plane mirror 3 and the optical spot position detection element 4 are disposed in a plane in the X direction, an error in the Y direction is smaller than an error in the X direction.

FIG. 6B is a graph showing results when the reference angle is (θx, θy)=(10°,5°), that is, when the position of the pupil 31 is upper right from the normal vision. The rotation angle of the eyeball 30 is estimated within an error range that is equivalent to the result of FIG. 6A.

The results of the numerical simulation described above show estimated values of the rotation angle of the eyeball 30. The rotation angle of the eyeball 30 can be defined as the angle formed by the Z-axis, which is the direction of normal vision, and a line connecting the center of the eyeball 30, that is, the rotation center position to the center position of the cornea. The position of the pupil 31 can thus be calculated as a coordinate that is apart from the center position of the eyeball 30 in the direction of the rotation angle of the eyeball 30 by the distance between the center position of the eyeball 30 and the center position of the cornea. The distance from the center position of the eyeball 30 to the center position of the cornea is given in advance by the eyeball model.

As described above, the numerical simulation verifies that the position of the pupil 31 can be calculated with sufficient accuracy by the calculation process of the pupil position calculator 120 illustrated in FIG. 5.

As described above, the present embodiment includes the light source array 1 including a plurality of light emitting sections for emitting light having directivity and the detection element for detecting the position of light reflected from the light emitting sections on an eyeball. By changing the light emitting sections of the light source array 1 at a predetermined time, the incident angle of light on the eyeball 30 is changed and the range of detecting the position of the pupil 31 is extended. In the present embodiment, such pupil position detection is performed by a non-mechanical structure without using a movable structure such as a MEMS mirror. It is thus possible to achieve pupil position detection that is resistant to vibration and external impact. In other words, according to the present embodiment, it is possible to provide an eyeball-tilt-position detector such as a pupil position detector that is resistant to vibration and external impact.

As the present embodiment does not include a movable part such as a MEMS mirror, it is possible to reduce the amount of light that is reflected from the eyeball but does not reach a photodetector and thus improve light use efficiency. In addition, it is possible to reduce the influence of noise such as surrounding ambient light. Moreover, there is no dynamic deformation as in a MEMS mirror and thus it is possible to secure the detection accuracy of a pupil position without any complicated adjustments.

According to the present embodiment, a two-dimensional PSD or a one-dimensional PSD is used as the optical spot position detection element 4 to detect the incident position of light that is irradiated on the eyeball and reflected from the eyeball on the light receiving surface of the optical spot position detection element 4. It is possible to detect the position of incident light independently of the intensity of the incident light. If there is a difference in the amount of reflected light due to the light reflection position on the eyeball 30 or the like, it is possible to detect the position of incident light with high sensitivity without being affected by the difference in the amount of reflected light. Consequently, it is possible to detect the tilt position of the eyeball such as the pupil with high accuracy.

As the image sensor such as a CCD is not used for detecting the position of incident light, a load of processing such as image processing can be reduced. Further, it is possible to achieve high-speed and real-time detection of the pupil position or the like without using expensive devices including a high-speed computing unit and a high capacity memory. When the one-dimensional PSD is used as the optical spot position detection element 4, it is possible to achieve an eyeball-tilt-position detector such as a pupil position detector at low cost.

According to the present embodiment, the light source array 1 and the lens 2 are disposed on the same substrate to be integrated with each other. It is thus possible to downsize the eyeball-tilt-position detector and to reduce a load of assembling the eyeball-tilt-position detector. A first substrate on which the light source array 1 is disposed and a second substrate on which the lens 2 is disposed may be brought into contact with each other to be integrated with each other, for the purpose of achieving the effects described above.

A VCSEL is used for the light source array 1 in the present embodiment. By changing the light emitting section of the VCSEL, the incident angle of light on the eyeball 30 can be changed and the range of detecting the position of the pupil 31 can be extended.

While an example of a configuration including one light source array 1 is described above, it may be configured to include a plurality of light source arrays. In this case, the range in which the incident angle of light on the eyeball 30 is changed can be further extended and the range of detecting the position of the pupil 31 can be also further extended.

Second Embodiment

Next, a pupil position detector according to a second embodiment will be described with reference to FIG. 7. In the second embodiment, descriptions of the same components as those of the previously described embodiment will be omitted.

Figure 7:
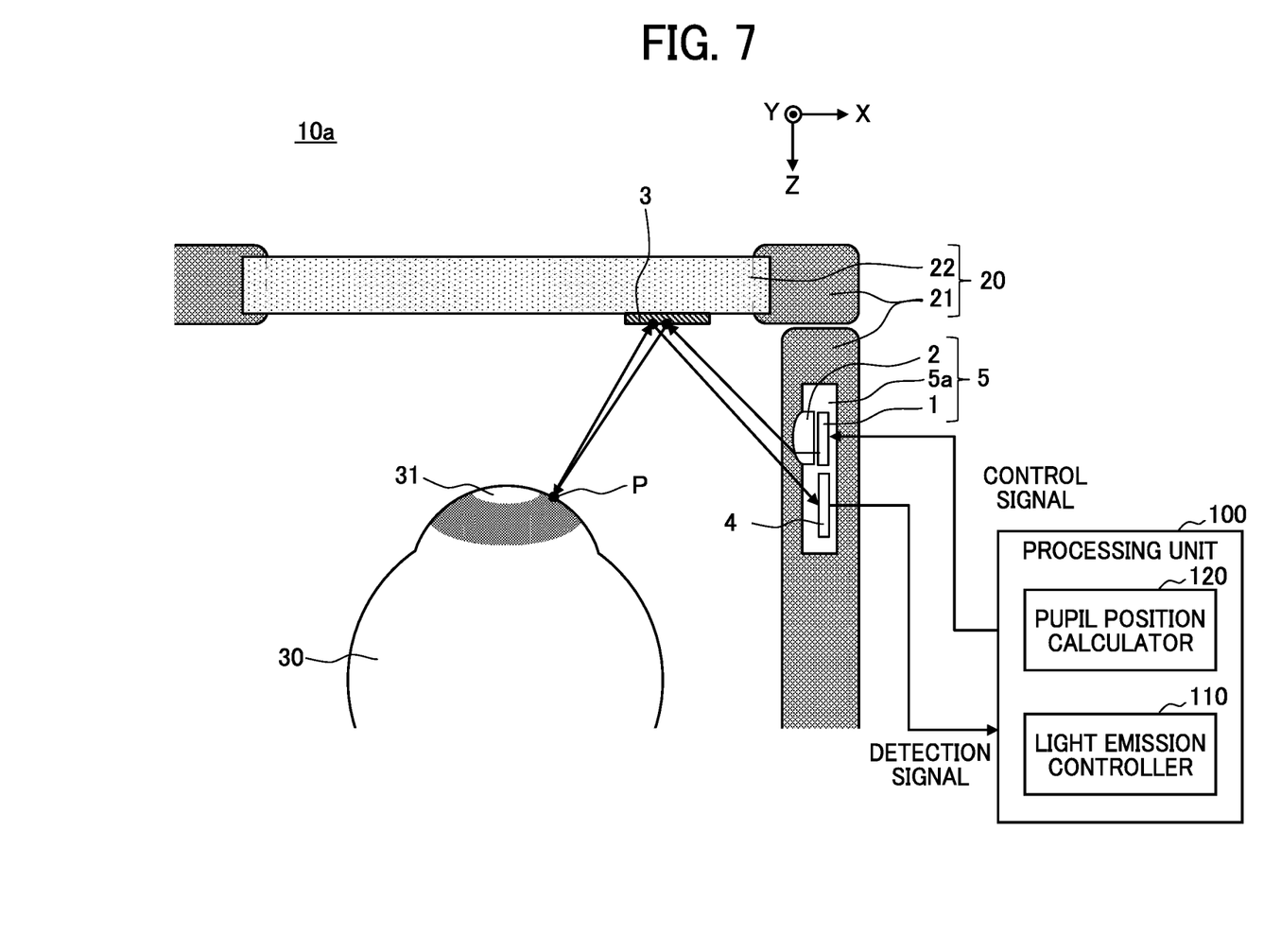
FIG. 7 is a view illustrating an example of a configuration of a pupil position detector according to a second embodiment.

FIG. 7 is a view illustrating an example of a configuration of a pupil position detector 10a according to the present embodiment.

In the pupil position detector 10a, the optical spot position detection element 4 is disposed in a direction in which light incident on the eyeball 30 via the light source array 1 and the lens 2 is retroreflected. That is, the optical spot position detection element 4 is disposed on the same side of the eyeball 30 as the light source array 1.

The incident position of light on the eyeball 30 and the position of the reflection point P are different from those of the first embodiment, so that the optical spot position detection element 4 is disposed as described above.

According to the present embodiment, the light distribution module 5 including the light source array 1, the lens 2, and the substrate 5a can be disposed on the same substrate as the optical spot position detection element 4, and thus the light distribution module 5 and the optical spot position detection element 4 can be integrated with each other. As the relative position of the light distribution module 5 and the optical spot position detection element 4 does not change, it is not necessary to adjust the positions of the light distribution module 5 and the optical spot position detection element 4.

Other effects are similar to those described in the first embodiment.

Third Embodiment

Next, a pupil position detector according to a third embodiment will be described with reference to FIGS. 8A through 9. Descriptions of the same components as those of the first and second embodiments previously described will be omitted.

While the first and second embodiments have described the example of using the lens 2 and the plane mirror 3 as the light deflector, the present embodiment describes an example of deflecting light by other methods.

Figure 8A:
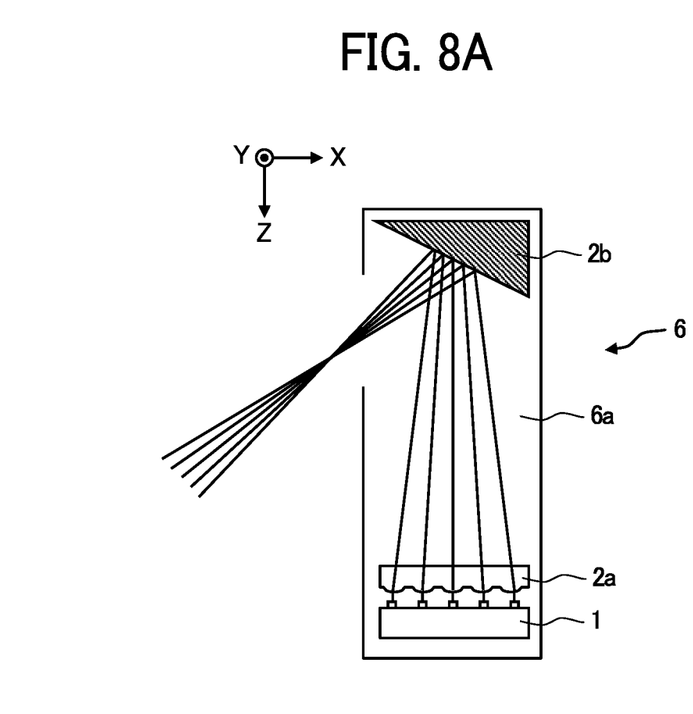
FIGS. 8A and 8B are views illustrating examples of a light deflector according to a third embodiment.

FIG. 8A illustrates an example of a light deflector including a microlens array 2a and a reflecting mirror 2b. A light distribution module 6 includes the light source array 1, the microlens array 2a, the reflecting mirror 2b, and a substrate 6a.

As illustrated in FIG. 8A, each light emitting section of the light source array 1 and each lens of the microlens array 2a are arranged to correspond to each other. In addition, the light emitting sections are arranged to be shifted in the X-axis direction and the Y-axis direction with respect to the optical axes of the lenses of the microlens array 2a, and the shift amount is different for each light emitting section. The deflection angle of light from the light emitting section is adjusted by the shift amount.

As the substrate having the microlens array 2a formed thereon is brought into contact with and disposed on the substrate of the light source array 1, it is possible to downsize the light distribution module 6 and reduce the thickness of the light distribution module 6. In addition, it is possible to easily adjust the deflection angle of light from the light emitting section with high accuracy. In other words, it is possible to easily adjust the incident angle of light on the eyeball 30 with high accuracy. The light distribution module 6 includes the reflecting mirror 2b to allow light to return, and thus optical components to be mounted including the microlens array 2a can be simplified.

Figure 8B:
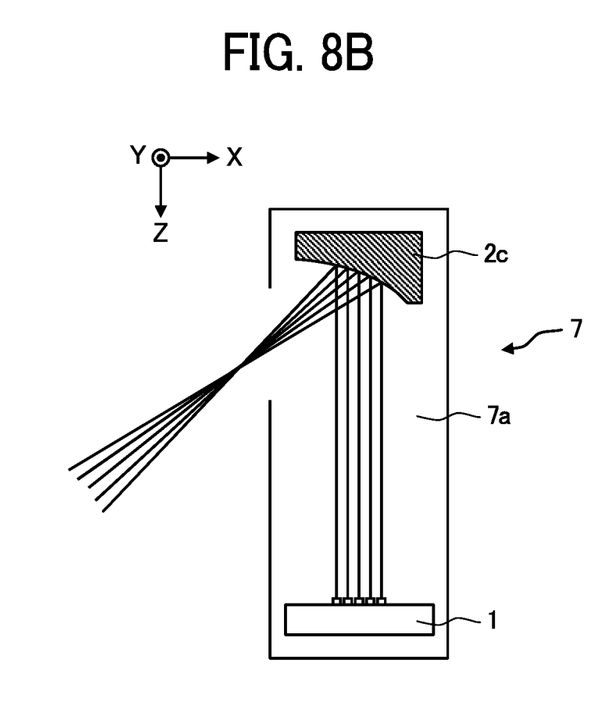

FIG. 8B illustrates an example of a light deflector including a concave curved mirror 2c. A light distribution module 7 includes the light source array 1, the concave curved mirror 2c, and a substrate 7a. As the concave curved mirror 2c is included, it is possible to reduce the number of optical components, allow light to return, and simplify the optical components to be mounted.

In addition to the components described above, a diffraction grating, a prism, a hologram element and the like can be used as the light deflector. The diffraction grating and the prism are basically one-dimensional deflection elements. For this reason, when the diffraction grating or the prism is used as the light deflector, it is necessary to use two or more diffraction gratings or two or more prisms whose deflection directions cross with each other in combination, or to form an area dividing structure on the deflecting surface of the diffraction grating or the prism for the purpose of deflecting light in two or more crossing directions.

Figure 9:
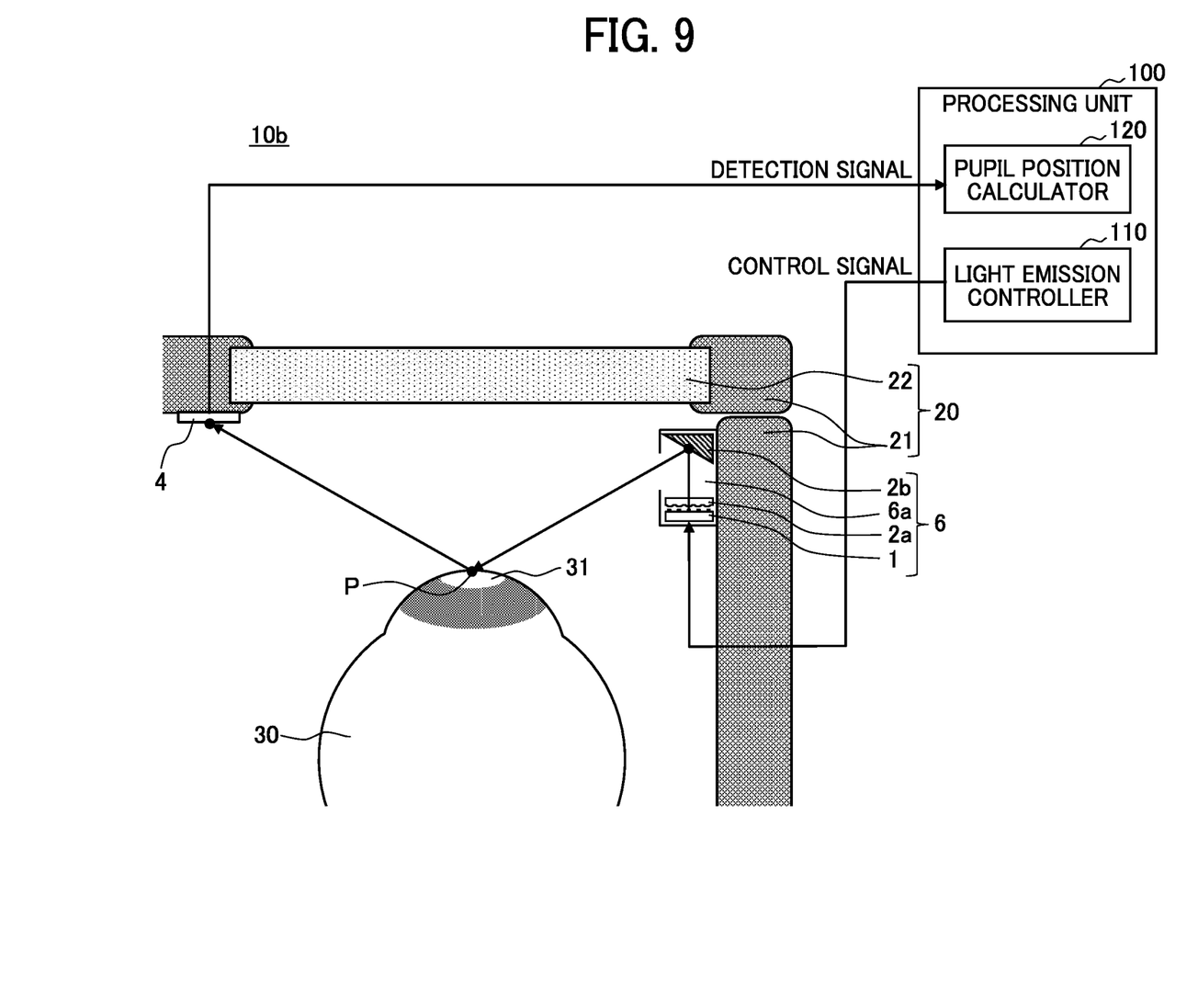
FIG. 9 is a view illustrating an example of a configuration in which a light distribution module according to the third embodiment is disposed on an eyeglasses-type support.

FIG. 9 illustrates an example of a configuration in which the light distribution module 6 illustrated in FIG. 8A is formed on the eyeglass-type support 20. While the optical spot position detection element 4 is disposed on the eyeglass frame 21 in FIG. 9, the position where the optical spot position detection element 4 is disposed is not limited. It is only required that the optical spot position detection element 4 is disposed in a manner that reflected light from the eyeball 30 is incident on the light receiving surface of the optical spot position detection element 4.

According to the present embodiment, the light deflector is any one of a convex lens region, a plane mirror, a microlens array, a concave curved mirror, a hologram diffraction element, a prism array, and a diffraction grating, or two or more combinations of these components. It is thus possible to change the incident angle of light on the eyeball 30 and extend the range of detecting the position of the pupil 31. As light is deflected by a simple structure that does not include a movable part, it is possible to downsize an eyeball-tilt-position detector and to reduce a load of assembling the eyeball-tilt-position detector.

According to the present embodiment, the light source array 1 and the light deflector such as the microlens array are disposed on the same substrate to be integrated with each other. It is thus possible to downsize the eyeball-tilt-position detector and to reduce a load of assembling the eyeball-tilt-position detector. A substrate on which the light source array 1 is disposed and a substrate on which the light deflector such as the microlens array 2a is disposed may be brought into contact with each other to be integrated with each other, for the purpose of achieving the effects described above.

Other effects are similar to those described in the first and second embodiments.

Fourth Embodiment

Next, a display apparatus according to a fourth embodiment will be described with reference to FIG. 10. Descriptions of the same components as those of the first through third embodiments previously described will be omitted.

Figure 10:
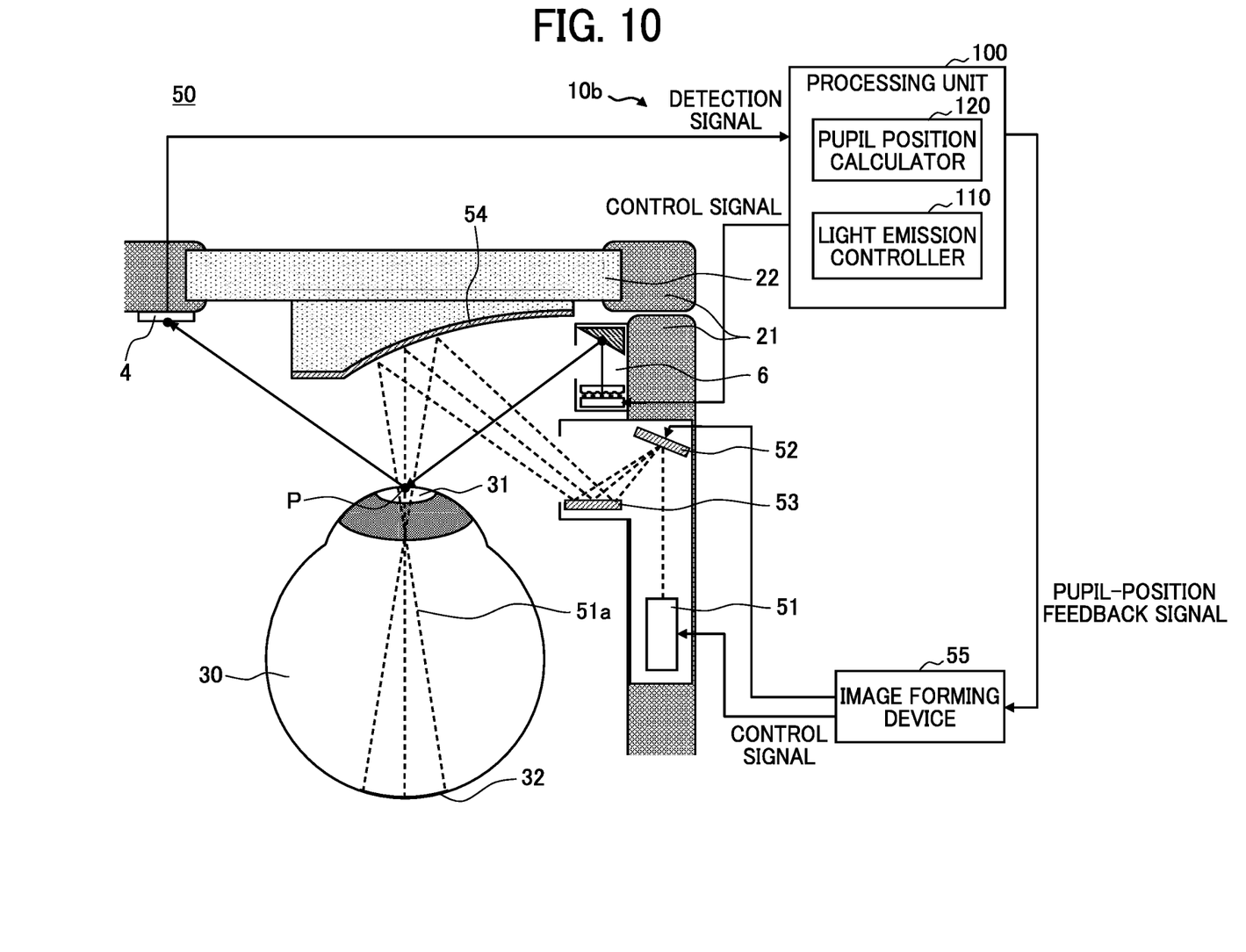
FIG. 10 is a view illustrating an example of a configuration of a display apparatus according to a fourth embodiment.

FIG. 10 is a view illustrating an example of a configuration of a display apparatus 50 according to the present embodiment.

The display apparatus 50 includes an RGB (Red, Green, Blue) laser light source 51, a scanning mirror 52, a plane mirror 53, a half mirror 54, an image forming device 55, and the pupil position detector 10b.

The RGB laser light source 51 temporally modulates three RGB colors of laser light and outputs the modulated laser light. The scanning mirror 52 two-dimensionally scans light from the RGB laser light source 51. The scanning mirror 52 is, for example, a MEMS mirror. Any mirror that has a reflecting part for scanning light such as a polygon mirror and a galvanometer mirror may be used as the scanning mirror 52. The MEMS mirror is advantageous because of its compactness and reduced weight. The drive system of the MEMS mirror may be an electrostatic system, a piezoelectric system, or an electromagnetic system.

The plane mirror 53 reflects light scanned by the scanning mirror 52 to the half mirror 54. The half mirror 54 transmits a part of incident light and reflects another part of incident light to the eyeball 30. The half mirror 54 has a concave curved shape, converges reflected light near the pupil 31 of the eyeball 30, and forms an image on a retina 32. An image formed by scanning light is thus projected onto the retina 32. Light 51a indicated by broken lines in FIG. 10 represents light forming an image on the retina 32. It is not necessary that the ratio of the light amount of reflected light to the light amount of transmitted light is 1:1 in the half mirror 54.

The pupil position detector 10b detects the position of the pupil 31 according to eye movements and transmits a feedback signal indicating the position of the pupil 31 to the image forming device 55.

The image forming device 55 has a function of controlling the deflection angle of the scanning mirror 52 and a function of controlling light emission of the RGB laser light source 51. The image forming device 55 also receives the feedback signal indicating the position of the pupil 31 from the pupil position detector 10b. Based on the position of the pupil 31 detected by the pupil position detector 10b, the image forming device 55 controls the deflection angle of the scanning mirror 52 and the light emission of the RGB laser light source 51 and rewrites the projection angle of an image or the image content. It is thus possible to form an image acquired by tracking (eye-tracking) changes in the position of the pupil 31 according to eye movements on the retina 32.

The above description is an example of using a head mount display (HMD), which is a wearable terminal, as the display apparatus 50. The display apparatus 50 serving as a head mounted display may be not only directly attached to the head of person but also indirectly attached to the head of person via a member such as a fixing part. Alternatively, a binocular display apparatus having a pair of display apparatus 50 for left and right eyes may be used.

Figure 11:
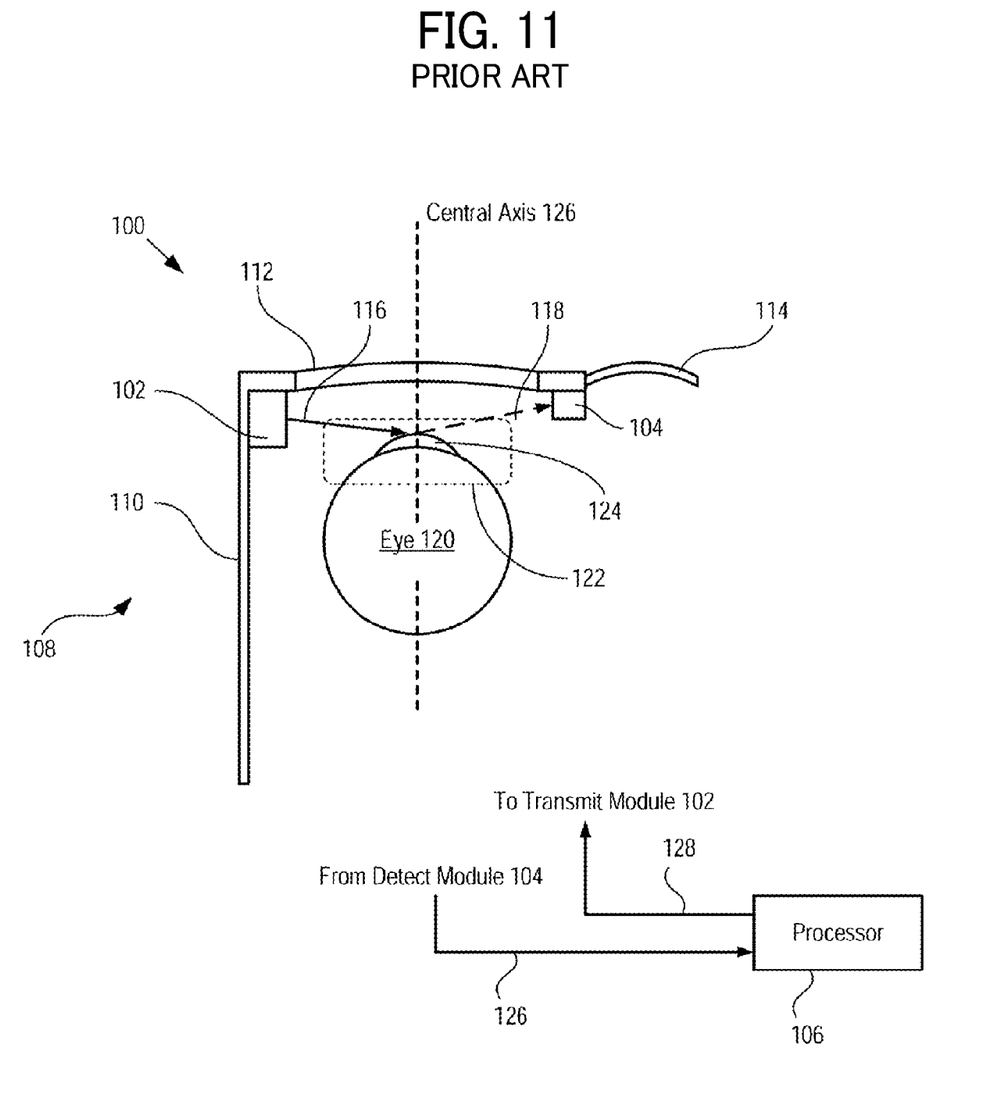
FIG. 11 is a view illustrating a configuration of an eye tracking apparatus according to the related art.

Next, the apparatus described in the related art, in particular, the one described in U.S. Patent Application Publication No. 2016/0166146A1, is compared to the pupil position detectors 10, 10a, and 10b according to the present embodiments. FIG. 11 is a view illustrating a configuration of an eye tracking apparatus described in the above-described publication.

The apparatus described in the above-described publication uses a laser light source to scan laser light using a MEMS mirror and changes the incident angle of light on an eye 120. On the other hand, in the present embodiment, the light source array 1 having a plurality of light emitting sections is used as a light source and the incident angle of light on the eyeball 30 is changed by changing the light emitting sections of the light source array 1. In the present embodiment, by using the light deflector (a lens, a plane mirror, a microlens array, a concave curved mirror, a hologram diffraction element, a prism array, a diffraction grating, or the like) together with the light source array 1, the range of changing the incident angle is extended. In the present embodiment, the incident angle of light on the eyeball 30 is changed without using a movable part, as described above. Consequently, one or more embodiments of the present invention area more resistant to vibration and external impact than a structure including a movable part.

In the apparatus described in the above-described publication, the intensity of light irradiated on a cornea and reflected from the cornea is detected by a photodetector. On the other hand, in the present embodiment, the optical spot position detection element 4 such as a two-dimensional PSD is used to detect the position of light reflected from the eyeball 30 and incident on the light receiving surface of the optical spot position detection element 4. The PSD detects the position of incident light independently of light intensity. Consequently, if there is a difference in the amount of reflected light due to the light reflection position on the eyeball 30 or the like, it is possible to detect the position of incident light with high sensitivity without being affected by the difference in the amount of reflected light. As a result, it is possible to detect the tilt position of the eyeball such as the pupil with high accuracy.

The present embodiment includes the light emission controller 110, and the light emitting sections of the light source array 1 are individually turned on by the light emission controller 110 shifting the position of the light emitting section to be turned on and the light emission time of the light emitting section. It is thus possible to capture fluttering of the eyeball 30 to cause reflected light from the eyeball 30 to be incident on the light receiving surface of the optical spot position detection element 4. In addition, it is possible to capture fine movements of the eyeball 30 with position detection by the optical spot position detection element 4.

In the apparatus described in the above-described publication, the position of the eyeball is estimated from two peak intensities (two reflection positions on the cornea) on the time axis of reflected light on the eyeball. In the present embodiment, the position of the eyeball is estimated from one reflection position on the eyeball such as the cornea. For this reason, the position of the light source array 1 does not need to be symmetrical to the position of the optical spot position detection element 4. In the present embodiment, the optical spot position detection element 4 may be disposed not at near the regular reflection (specular reflection) angle of the eyeball 30 but on the same side as the light source array 1.

While the pupil position detector and the display apparatus including the pupil position detector according to the embodiments have been described above, the present invention is not limited to the embodiments described above, and various alterations and modifications are possible within the scope of the present disclosure.

In alternative to the display apparatus, the pupil position detector according to one or more embodiments described above can be used for an eye examination apparatus that has a function of detecting the tilt of an eyeball and the position of a pupil (cornea). The eye examination apparatus refers to an apparatus capable of performing various inspections including an eye test, an eye refraction test, a tonometry test, and an axial length test. The eye examination apparatus can perform in inspections without contacting the eyeball, and includes a support part for supporting a subject's face, an inspection window, a display that displays the eyeball while the direction of the subject's eyeball (gaze direction) is fixed during an eye inspection, a controller, and a measurement device. To improve the measurement accuracy of the measurement device, the subject is required to look at one point without moving the eyeball (gaze). The subject gazes at a display object on the display from the inspection window, while the subject's face is fixed on the support part. In this case, when the tilt position of the eyeball is detected, the eyeball-tilt-position detector according to the present embodiment can be used. The eyeball-tilt-position detector is disposed on the side of the measurement device so as not to disturb measurements. Information about the tilt position of the eyeball (gaze) acquired by the eyeball-tilt-position detector can be fed back to the controller such as a CPU. Under control of the CPU, the measurement device performs measurements based on the info, illation about the tilt position of the eyeball.

The above-described embodiments are illustrative and do not limit the present invention. Thus, numerous additional modifications and variations are possible in light of the above teachings. For example, elements and/or features of different illustrative embodiments may be combined with each other and/or substituted for each other within the scope of the present invention.

Any one of the above-described operations may be performed in various other ways, for example, in an order different from the one described above.

Each of the functions of the described embodiments may be implemented by one or more processing circuits or circuitry. Processing circuitry includes a programmed processor, as a processor includes circuitry. A processing circuit also includes devices such as an application specific integrated circuit (ASIC), digital signal processor (DSP), field programmable gate array (FPGA), and conventional circuit components arranged to perform the recited functions.

The invention claimed is:

1. An eyeball-tilt detecting device for detecting a rotation angle of an eyeball, comprising:
    a light source array including a plurality of light emitting sections that emit light having directivity;
    a light deflector that causes the light to be incident on the eyeball at a predetermined angle;
    an optical spot position detector configured to detect an optical spot position of light reflected from the eyeball to output a detection signal; and
    processing circuitry configured to calculate the rotation angle of the eyeball based on the detection signal output from the optical spot position detector.

2. The eyeball-tilt detecting device according to claim 1, wherein the processing circuitry is further configured to control a light emission time when one or more of the light emitting sections of the light source array emit light.

3. The eyeball-tilt detecting device according to claim 2, wherein the processing circuitry is further configured to change the light emission time of the one or more light emitting sections at a predetermined time.

4. The device according to claim 1, wherein the light source array includes a surface emitting laser in which the light emitting sections are arranged in a plane.

5. The eyeball-tilt detecting device according to claim 1, wherein the optical spot position detector includes a two-dimensional position sensitive detector (PSD).

6. The eyeball-tilt detecting device according to claim 1, wherein the optical spot position detector includes a plurality of one-dimensional PSDs arranged in a predetermined direction.

7. The eyeball-tilt detecting device according to claim 1, wherein
    the light deflector is at least one of a convex lens region, a plane mirror, a microlens array, a concave curved mirror, a hologram diffraction element, a prism array, and a diffraction grating.

8. The eyeball-tilt detecting device according to claim 6, wherein the light source array and the light deflector are disposed on a same substrate.

9. The eyeball-tilt detecting device according to claim 6,
    wherein the light source array is disposed on a first substrate and the light deflector is disposed on a second substrate, and
    the first substrate and the second substrate are disposed to contact each other.

10. The eyeball-tilt detecting device according claim 1, further comprising a light deflector that causes the light to be incident on the eyeball at a predetermined angle, wherein the light source array and the light deflector are disposed on a same substrate.

11. The eyeball-tilt detecting device according to claim 1, wherein the optical spot position detector is disposed on a same side of the eyeball as the light source array.

12. A display apparatus, comprising:
    the eyeball-tilt detecting device according to claim 1; and
    an image forming device configured to control forming of an image based on the rotation angle of the eyeball.

13. An eye examination apparatus, comprising:
    the eyeball-tilt detecting device according to claim 1; and
    a measurement device configured to perform measurements based on information on the rotation angle of the eyeball.

14. The eyeball-tilt detecting device of claim 1, wherein the processing circuitry is further configured to calculate a center position of a pupil based on the calculated rotation angle.

15. The eyeball-tilt detecting device of claim 1, wherein the processing circuitry is configured to calculate the rotation angle of the eyeball based on the optical spot position using a predetermined function.

* * * * *